United States Patent
Ito et al.

(10) Patent No.: US 6,375,974 B1
(45) Date of Patent: Apr. 23, 2002

(54) PROCESS FOR PRODUCING AQUEOUS SOLUTION OF FUMARIC ACID

(75) Inventors: Toshio Ito, Tokyo; Yukio Tanaka, Osaka, both of (JP)

(73) Assignee: Mitsui Takeda Chemicals, Inc., Osaka (JP)

( * ) Notice: Subject to any disclaimer, the term of this patent is extended or adjusted under 35 U.S.C. 154(b) by 0 days.

(21) Appl. No.: 09/471,253

(22) Filed: Dec. 23, 1999

(30) Foreign Application Priority Data

Dec. 24, 1998 (JP) .......................................... 10-367003
Dec. 28, 1998 (JP) .......................................... 10-372785

(51) Int. Cl.$^7$ ................................................ A61F 13/00
(52) U.S. Cl. ...................................... 424/434; 424/457
(58) Field of Search ............................. 424/434, 457; 71/21

(56) References Cited

U.S. PATENT DOCUMENTS

| | | | | |
|---|---|---|---|---|
| 4,405,354 A | * | 9/1983 | Thomas, II et al. | ............ 71/21 |
| 5,403,548 A | | 4/1995 | Aibe et al. | |
| 5,589,186 A | | 12/1996 | Isobe et al. | |
| 5,603,945 A | | 2/1997 | Isobe et al. | |

OTHER PUBLICATIONS

Product Alert, "Vanish Hang–Ins Automatic Toilet Bowl", Mar. 10, 1997.*
Product Alert, "SC Johnson & Son to Introduce Vanish Drop Ins", Oct. 11, 1993.*
Derwent Abstract for JP–A–06–126166.
Derwent Abstract for JP–A–59–151963.
Derwent Abstract for JP–A–52–063882.
J. Food Protection, 59 (4), 370–373 (1996).

\* cited by examiner

Primary Examiner—Jose' G. Dees
Assistant Examiner—Robert M DeWitty
(74) Attorney, Agent, or Firm—Birch, Stewart, Kolasch & Birch, LLP

(57) ABSTRACT

A process for obtaining an aqueous fumaric acid solution which is useful in stably obtaining a large amount of aqueous fumaric acid solution. A column is packed with solid fumaric acid and then water is passed through the column, thereby giving an aqueous fumaric acid solution. Water is usually passed in the reverse direction. The solid fumaric acid may be in the form of tablets containing 70% by weight or more of fumaric acid. The aqueous fumaric acid solution thus obtained has a pH value of about 1 to 4. A urinal, etc. is treated with a fumaric acid-containing deodorizing agent to thereby efficiently deodorize nitrogen-containing bad-smelling components over a long period of time. A solid deodorizing agent containing fumaric acid, which has an extremely low solubility and a low dissolution rate in water, is placed on a urinal to deodorize the same.

9 Claims, 2 Drawing Sheets

PROCESS FOR PRODUCING AQUEOUS SOLUTION OF FUMARIC ACID

FIELD OF THE INVENTION

This invention relates to a process which is useful for stably and continuously obtaining a large amount of an aqueous fumaric acid solution and tablets and a column to be used therein. The invention further relates to a deodorization method which is useful in deodorizing bad-smelling components over a long period of time in a toilet, etc.

BACKGROUND OF THE INVENTION

Compared with other organic acids, fumaric acid exerts a strong antibacterial effect on various gram negative bacteria within a short time. Based on the showing of a strong bactericidal effect on *Escherichia coli* O-157 which has caused health concerns recently, fumaric acid is expected to be highly useful. In addition, fumaric acid, which is an organic acids contained in natural substances such as rice and mushrooms, is a food additive with no restrictions on use. Thus, it has been employed as a highly safe bactericide.

On the home page (dated Jul. 11, 1997) of Niigata Pref. Central Research Institute, it was reported that a mixture of 0.2% of fumaric acid with 0.2% of ascorbic acid showed a bactericidal effect on salmonella, coliform, enteritis vibrio and yeasts other than gram negative ones. It was also reported that when fumaric acid (0.02 to 0.20%) containing 0.05% of ascorbic acid was compared in bactericidal efficacy with ethanol, ethanol exerted a bactericidal effect after 60 minutes while fumaric acid (0.2%) exerted a comparable effect after 1 minute.

It was reported in "Shoku Ei Shi" (J. of Food Sanitation) Vol. 36, No. 1, p. 50–54 that fumaric acid inhibited the growth of gram negative bacteria; but that fumaric acid was minimally soluble in water at room temperature and a 0.3 % aqueous solution thereof was of little use because of undergoing precipitation at 4° C. Further, an aqueous solution of monosodium fumarate having a high solubility did not show bactericidal effects at a concentration of 0.6% or less but rather at 0.8%.

On the other hand, the Journal of Food Protection, Vol. 1, 59, No.4, 1996 (370–373) reported bactericidal effects of organic acids including fumaric acid on various bacteria such as *E. coli* 0–157. According to this document, fumaric acid exhibited a bactericidal effect exceeding those of other organic acids at 1.0% and 1.5%.

When fumaric acid is used as a bactericide, it has been a practice to dissolve solid fumaric acid in water, etc. to give an aqueous fumaric acid solution. However, fumaric acid shows only a low solubility, i.e., 0.2 to 0.5 g per 100 cc of water at 10 to 20° C. The solubility of fumaric acid can be only be minimally improved even at higher temperatures (i.e., 1.6 g at 50° C. and 5.25 g at 80° C.). Also, fumaric acid has a low dissolution rate. To obtain an aqueous fumaric acid solution, it is therefore necessary to increase its solubility by heating to a definite temperature and then diluting the thus obtained solution, or to forcibly stir the mixture over a long period of time, thus taking a long time and costing much. That is to say, it is very difficult to economically produce a large amount of an aqueous fumaric acid solution within a short time. It is also impossible to obtain an aqueous fumaric acid solution having a high concentration.

Because of the low dissolution rate, fumaric acid cannot be completely dissolved but remains as fine grains giving a slurry in these conventional methods. When 15 g of fine fumaric acid grains (80-mesh pass) are added to 10 l of water at 20° C. (i.e., a 0.15% aqueous fumaric acid solution) and slowly stirred for 24 hours, for example, the fine grains are not completely dissolved but partly remain as such. When such an aqueous fumaric acid solution is employed in sterilizing vegetables, etc., the remaining grains adhere to the surface of the vegetables and the fumaric acid at a high concentration causing a partial color change in the vegetables, thus lowering the commercial value thereof. When such an aqueous fumaric acid solution is employed in sterilizing meats, the remaining fumaric acid grains sometimes damage the meat tissue.

A method for obtaining an aqueous fumaric acid solution by adding sodium fumarate or surfactants, which have a high dissolution rate, to fumaric acid having a poor dissolution rate to thereby elevate the dissolution rate as the whole. However, the aqueous fumaric acid/sodium fumarate solution thus obtained is inferior in bactericidal effect to an aqueous fumaric acid solution.

As discussed above, although fumaric acid shows an excellent bactericidal effect, it has low solubility and a low dissolution rate, which makes it impossible to efficiently obtain an aqueous fumaric acid solution having a high concentration (pH 1 to 4).

Granular active carbon and honeycomb active carbon have been employed in eliminating bad-smelling gases in sources and facilities which produce or emit offensive smells, for example, sewage disposal plants, sludge processing plants, fecal disposal plants, cattle farms and garbage processing plants. To elevate the deodorization efficiency, it has been also proposed to use active carbon honeycombs carrying citric acid, alkali metal citrates, etc. thereon (JP-A-59-151963; the term "JP-A" as used herein means an "unexamined published Japanese patent application"), honeycombs having acids such as sulfuric acid or alkalis adhered thereto (JP-A-52-63882), honeycombs carrying alkali metal iodides and phosphoric acid thereon (JP-A-6-126166), etc. When these active carbon products are used in deodorizing toilets, in particular, urinals, the deodorizing ability of active carbon is very deteriorated by urinary spray.

Alternatively, aromatic odor-masking agents have been employed in urinals. However, these masking agents cannot deodorize ammonia and amines. Moreover, these masking agents dissolve in urine and thus fail to efficiently eliminate the offensive smells of ammonia and amines over a long time.

SUMMARY OF THE INVENTION

Accordingly, an object of the present invention is to provide a process for efficiently producing an aqueous fumaric acid solution having a high safety and an excellent bactericidal effect and tablets and a column therefor.

Another object of the present invention is to provide a process for producing a large amount of an aqueous fumaric acid solution having a high concentration within a short period of time and tablets and a column therefor.

Another object of the present invention is to provide a deodorization method with the use of a solid deodorizing agent which is useful in deodorizing over a long period of time.

Another object of the present invention is to provide a deodorization method which is useful in efficiently deodorizing nitrogen-containing bad-smelling components in a urinal over a long period of time. The present inventors have focused their studies to the fact that fumaric acid shows a very low solubility and a low dissolution rate in water. As the result of intensive studies to achieve the above-described objects, the present inventors have found that an aqueous fumaric acid solution can be stably and continuously obtained by passing water through a column packed with solid fumaric acid. They have further found out that nitrogen-containing bad-smelling components (ammonia, amines, etc.) can be efficiently deodorized over a long period of time by placing a solid preparation containing fumaric acid in a urinal. The present invention has been completed based on these findings.

In the present invention, therefore, an aqueous fumaric acid solution is produced by passing water through a column packed with solid fumaric acid. Water may be passed downward or vice versa. The solid fumaric acid may be in the form of, for example, tablets containing 70% by weight or more (e.g., from 70 to 100% by weight) of fumaric acid.

Although water may be passed through the column, it is also possible to pass an aqueous solution therethrough. The water is not particularly limited and is exemplified by distilled water, purified water, tap water, etc., while the aqueous solution is exemplified by urine, water containing urine, an aqueous solution containing ammonia, etc.

The present invention involves within the scope thereof, a column packed with tablets or solid fumaric acid which are to be used to obtain an aqueous fumaric acid solution.

The present invention further provides a deodorizing agent made of a solid agent containing fumaric acid and a deodorization method. This deodorizing agent, which contains fumaric acid in a solid state, is useful in deodorizing ammonia and amines. In particular, it is placed in a urinal or put into a tank of a tank type flush water closet to thereby deodorize and/or sterilize the same. The deodorizing agent may be in the form of tablets. It usually contains 70% by weight or more of fumaric acid.

Unless otherwise noted, the term "fumaric acid" to be used herein involves not only fumaric acid but also fumarates.

DETAILED DESCRIPTION OF THE INVENTION

Figure 1:
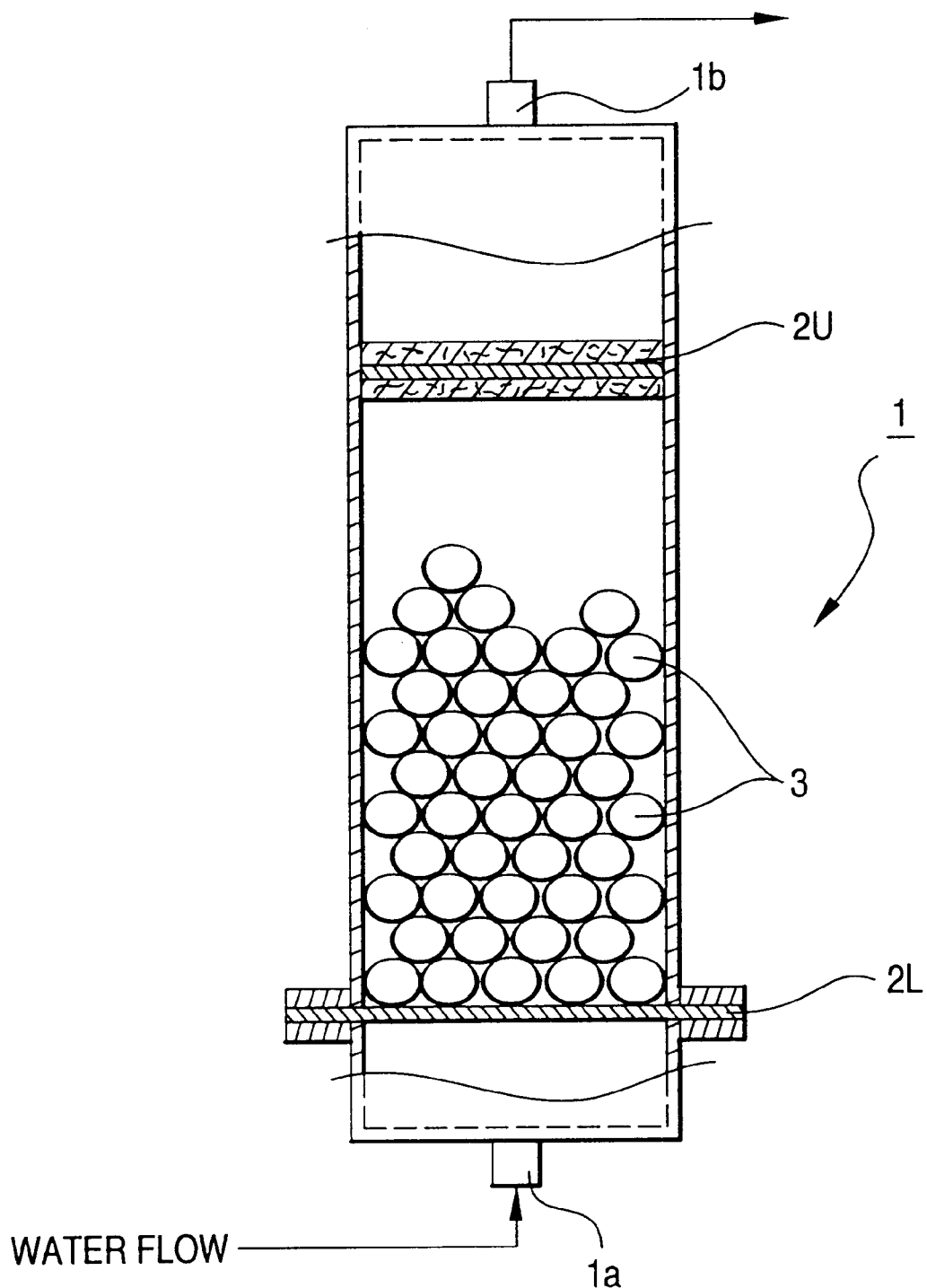
FIG. 1 shows a plane view of the column having a partial cross section of column.

Fumaric Acid:

Fumaric acid exerts a potent bactericidal effect on various gram negative bacteria (*E. coli*, salmonella, Shigella, etc.) within a short contact time. Because of being an organic acid which participates in the tricarboxylic acid (TCA) cycle, it is usable as a highly safe food additive with no restriction on use. Moreover, it can be easily obtained at a low price. However, fumaric acid is disadvantageous in having a low solubility and a low dissolution rate. For example, its solubility in 100 ml of water is as follows: 0.2 to 0.5 g (at 10 to 20° C.), 0.8 g (at 30° C.), 1.07 g (at 40° C.), 1.6 g (at 50° C.), 2.4 g (at 60° C.), 5.25 g (at 80° C.) and 9.8 g (at 100° C.).

In spite of these properties of fumaric acid, the process according to the present invention makes it possible to continuously and stably obtain a definite aqueous fumaric acid solution (e.g., about 0.05 to about 0.3 w/w % fumaric acid aqueous solution; pH: about 1 to 4) by passing water through a column packed with solid fumaric acid.

According to the present invention, it is also possible to efficiently deodorize a water closet over a long period of time by using a solid deodorizing agent containing fumaric acid while maintaining the deodorizing agent in the solid state.

The fumaric acid to be used in the present invention may be either fumaric acid alone or a mixture of fumaric acid with its derivatives (e.g., fumarates such as sodium fumarate).

The fumaric acid to be used in the present invention may be a combination of fumaric acid with other organic acids, for example, oxycarboxylic acids (tartaric acid, citric acid, malic acid, etc.) and ascorbic acid. In such a combination, the weight ratio of organic acid(s)/fumaric acid ranges from 0.01/1 to 1/1, preferably from 0.1/1 to 1/1.

The solid fumaric acid to be used in the present invention is not particularly restricted in form, so long as it is in a solid state. Namely, it may be in various forms such as powders (e.g., 20- to 200-mesh ones) or molded articles (tablets, granules, etc.). Since fumaric acid is adequate for tabletting, it is usually preferable to use the solid fumaric acid in the form of tablets.

The powders, granules or pellets may have an average diameter of from 0.1 to 100 mm, preferably from 0.5 to 50 mm.

When fumaric acid is used in the form of a powder, the leakage of the fumaric acid powder can be prevented by providing the inflow port and the outflow port of the column with meshes or filters capable of controlling the passage of the fumaric acid. Thus, the desired aqueous fumaric acid solution can be stably obtained.

When fumaric acid is used in the form of a molded article (e.g., tablets), it can be easily handled and packed into the column. In this case, moreover, the fumaric acid tablets being in contact with water are minimally dissolved from the surface, thereby regulating pH change and giving an aqueous fumaric acid solution having a definite pH value. If necessary, a fine mesh or filter may be provided at the upper part of the column to thereby prevent the aqueous solution from the contamination of the remaining solid fumaric acid grains.

A molded article of fumaric acid (e.g., tablets) can be prepared by using, if desired, additional components commonly employed in the art. Examples of these components for producing the molded article include fillers such as saccharides (sugar alcohols such as mannitol, xylitol and erythritol, disaccharides such as lactose, sucrose and sucrose ethers, corn starch, etc.), crystalline cellulose, silica, light anhydrous silicic acid, magnesium carbonate, calcium carbonate and cyclodextrin; water-soluble binders such as polysaccharides (cellulose ethers (hydroxypropyl cellulose, hydroxypropylmethyl cellulose, methyl cellulose, ethyl cellulose, hydroxymethyl cellulose, carboxymethyl cellulose, carboxymethyethyl cellulose, etc.), cellulose esters (cellulose acetate phthalate, hydroxypropyl methyl cellulose phthalate, etc.), α-starch, pullulan, dextrin, acacia, etc.), proteins such as gelatin and hydrophilic polymers (polyethylene glycol, Tween 80, acrylic copolymers, polyvinyl alcohol, polyvinyl pyrrolidone, polyvinyl acetal diethylamio acetate); and disintegrating agents such as carboxymethyl cellulose calcium, hydroxypropyl cellulose with low degree of substitution and starch. Among these components, it is preferable to use hydrophilic or water-soluble ones. In many cases, at least fillers are employed. Also, binders are used frequently.

The molded article containing fumaric acid may further contain various additives. Examples of these additives include surfactants such as anionic surfactants (sodium alkylsulfates, etc.) and nonionic surfactants (polyoxyethylene sorbitan fatty acid esters, polyoxyethylene fatty acid esters, polyoxyethylene alkyl phenol ethers, etc.); coloring matters such as red iron oxide and tar colorants; and perfumes. Since the dissolution rate of fumaric acid can be elevated by using a surfactant, the solubility and dissolution rate of fumaric acid can be controlled depending on the amount of the surfactant employed.

If necessary, the molded article may further contain shellac, waxes (paraffin wax, carnauba wax, beeswax, montan wax, etc.), fatty acids and salts thereof, aliphatic higher alcohols, castor oil and fatty acid glycerol esters and hardened oils thereof (hardened castor oil, hardened beef tallow, etc.).

The above-described molded article can be produced by a conventional method with the use of, for example, a kneader or a molding machine (extrusion molding machine, compression molding machine, etc.). Tablets can be produced by using a tabletting machine, etc.

The molded article (in particular, tablets) of fumaric acid contains fumaric acid in an amount of, for example, 70% by weight or more (e.g., from 70 to 100% by weight), preferably from 80 to 100% by weight and still preferably from 85 to 100% by weight (e.g., from 90 to 100% by weight). When the fumaric acid content is less than 70%, it is difficult to increase the dissolution of fumaric acid depending on the difference in solubility to thereby give an aqueous fumaric acid solution having a high concentration over a long period of time. In such a case, the molded article would be often disintegrated. In such a case, moreover, it is sometimes observed that the deodorizing performance of fumaric acid cannot be sustained over a long period of time. At the same time, the solid preparation becomes netty like a drainboard and may become broken due to a decrease in strength, thus causing clogging of a pipe, etc.

Water may be passed from the inflow flow or outflow flow provided respectively at the upper part and the lower part of the column in an arbitrary direction, i.e., either downward, upward or obliquely. It is preferable to pass water upward (i.e., the reverse flow from the lower part of the column to the upper part thereof) so that the short-pass of the water can be prevented and the fumaric acid can be brought into contact surely with the water at an increased efficiency. By using this reverse flow method wherein water is passed reversely, an aqueous fumaric acid solution having a high concentration can be efficiently obtained.

The column according to the present invention consists of the above-described solid fumaric acid (in particular, the tablets as described above) and a column provided with an inflow port and an outflow port. The inflow port is formed in the lower part of the column, namely, either at the bottom of the column or on the lower side wall thereof. The column according to the present invention may be further provided with meshes or filters. Usually, a fumaric acid packing chamber is formed between meshes or filters. It is also possible that the column consists of a column body into which the solid fumaric acid can be packed, an inflow port and/or filters, a cover which can be fitted into one end of the column body by sealing, an outflow port and/or filters and a cover which can be fitted into the other end of the column body by sealing. The column is usually in a cylindrical or cartridge form. To prevent short-pass, it is preferable that the column has the major axis in the vertical direction.

The size of the column is not particularly limited, but generally a size of from about 100 cm$^3$ to about 30 m$^3$ is preferable.

Figure 2A:
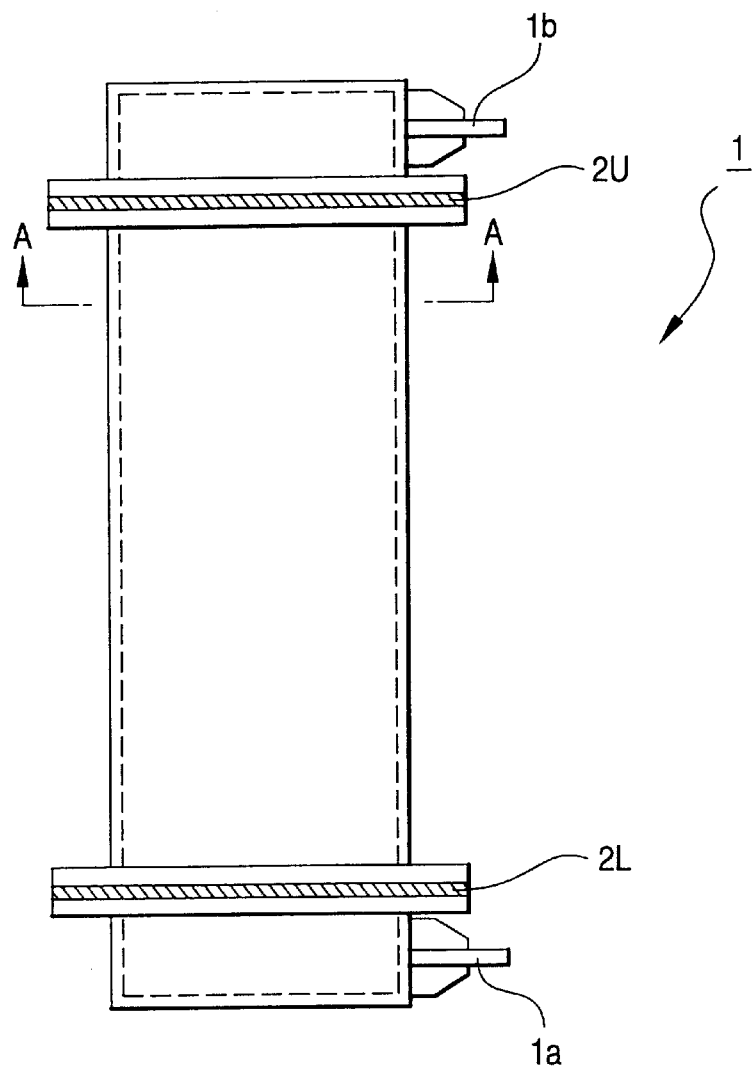
FIG. 2A shows a plane view of the colunmm and FIG. 2B is a cross section taken along line A—A of FIG. 2A.
Figure 2B:
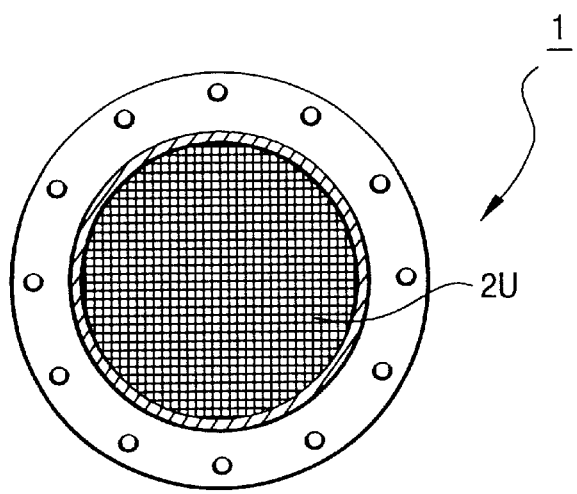

Examples of the column according to the present invention are shown in FIG. 1, FIG. 2A and FIG. 2B. In the drawings, 1 shows a column, 1$a$ shows an inflow port, 1$b$ shows an outflow port, 2U and 2L respectively show a mesh or filter, and 3 shows fumaric acid solids or tablets.

The flow rate of the water passing through the column packed with the solid fumaric acid ranges from 0.01 to 10 ml/min per gram of solid fumaric acid, preferably 0.05 to 7 ml/min and still preferably 0.1 to 5 ml/min. When the flow rate is 0.01 to 1 ml/min (e.g., 0.1 to 1 ml/min), an aqueous fumaric acid solution having a high concentration (i.e., a low pH value) can be obtained.

In the process according to the present invention, the solid fumaric acid may be optionally added to make up for the lost due to dissolution. The column may be packed with the solid fumaric acid at a ratio of from 50 to 95% by volume, preferably form 70 to 95% by volume and still preferably from about 80 to 90% by volume.

In a preferred embodiment of the present invention, tablets containing 70% by weight or more (in particular, about 90 to 100% by weight) of fumaric acid are packed into a column provided with an inflow port at the lower part and an outflow port at the upper part. Then water is passed from the inflow port to the outflow port (i.e., a reverse flow) at a rate of 0.01 to 10 ml/min per gram of fumaric acid and the aqueous fumaric acid solution overflowing from the outflow port is collected. By using this process, an aqueous fumaric acid solution having a high concentration (about pH 2 to 3) can be obtained.

According to the present invention, an aqueous fumaric acid solution having a high concentration and being free from any residual fumaric acid grain can be obtained. Therefore, the obtained aqueous fumaric acid solution shows a constant and stable pH value. The pH value of the aqueous fumaric acid solution thus obtained is from 1 to 4, preferably from 1.5 to 3.5 and more preferably from about 2 to 3. The pH value of the aqueous fumaric acid solution can be regulated to a desired level by diluting with water, etc., if needed.

The deodorization method according to the present invention is useful in deodorizing various bad-smelling components such as nitrogen-containing bad-smelling components (in particular, basic nitrogen-containing components). Examples of the nitrogen-containing bad-smelling components include ammonia and amines (mono-, di- and trialkylamines such as methylamine, dimethylamine, trimethylamine, diethylamine and triethylamine, cyclic amines, heterocyclic amines, etc.) The deodorizing agent according to the present invention is useful particularly in deodorizing nitrogen-containing bad-smelling components selected from among ammonia and alkylamines (trimethylamine, etc.). These bad-smelling components may further contain sulfur-containing bad-smelling components (hydrogen sulfide, mercaptans such as methylmercaptan and ethylmercaptan, sulfides such as methyl sulfide, disulfides such as methyl disulfide, etc.), aldehydes (formaldehyde, acetaldehyde, etc.), organic acids (formic acid, acetic acid, propionic acid, butyric acid, valeric acid, etc.), etc.

The concentration of the bad-smelling components is not particularly restricted but may range, for example, from 0.1 to 1,000 ppm on the weight basis, preferably from about 0.1 to 100 ppm.

The bad-smelling components can be deodorized by bringing the above-described deodorizing agent into contact with the substance to be treated which contains the bad-smelling components and which may be in the form of a gas, a liquid or a moistened solid. The deodorization may be carried out at a temperature of, for example, about 70° C. or below (e.g., −30 to 60° C.), preferably from about −20 to 50°

C. and more preferably from about -10 to 40° C. Usually, it is effected at about 0 to 40° C. (in particular, about 10 to 40° C. and preferably at room temperature of about 15 to 35° C).

The amount of the deodorizing agent to be used may be selected, depending on the content of fumaric acid, bad-smelling component concentration, etc., within a range of from about 1 mg to 100 g (preferably from about 10 mg to 50 g) in terms of fumaric acid per hour for a substance (urine, etc.) containing 1 to 1000 ppm of bad-smelling components (ammonia, etc.) to be treated.

The bad-smelling component source is not particularly restricted. Examples thereof include cattle farms (poultry housings, swine housings, cattle housings, etc.), small-sized rearing plants for experimental or test use in pharmaceutical companies, toilets (in particular, urinals and tanks in pool-type toilets such as tank type flush water closets), sewage disposal plants, sludge processing plants, fecal disposal plants and garbage processing plants. When the fumaric acid-containing deodorizing agent is poured into a rearing plant or fecal tank in an animal housing among the bad-smelling component sources as described above, the bad smells caused by ammonia, etc. can be eliminated over a long period of time and, at the same time, gram negative bacteria, etc. contained in the animal urine, etc. can be exterminated. When the deodorizing agent is placed in a tray, etc. in an animal rearing plant for test or experimental use, the ammonia smell, etc. can be relieved over a long period of time and sterilization can be established too.

When the deodorizing agent is placed in a urinal, the ammonia smell, etc. from the urine can be eliminated and, at the same time, the urine can be sterilized by bringing into contact with fumaric acid. When the deodorizing agent is applied to a toilet provided with an automatic flush device whereby water or washing liquor is intermittently (or periodically) supplied to the water closet, fumaric acid can be intermittently dissolved. In this case, therefore, the ammonia smell can be continuously eliminated and the washing and sterilizing effects can be enhanced merely by putting the deodorizing agent in the water closet.

In plants/devices wherein feces are washed with water or urinals provided with an intermittent or automatic flushing system, deodorization and sterilization can be performed by putting the deodorizing agent containing fumaric acid into the washing water pooled in a tank, etc. and using the thus formed aqueous fumaric acid solution as the washing liquor. In such a case, it is possible to use an aqueous fumaric acid solution produced by passing water through the above-described column packed with fumaric acid in washing and deodorization.

The aqueous fumaric acid solution produced by the process for producing an aqueous fumaric acid solution according to the present invention may further contain other organic acids (ascorbic acid, malic acid, tartaric acid, citric acid, etc.).

The aqueous fumaric acid solution obtained according to the present invention is not only has excellent safety and bactericidal effects but is also free from any grain remaining therein. Owing to these characteristics, it is usable in sterilizing foods (vegetables, meats, etc.), kitchen utensils, dishes, and walls and ceilings of places where foods are handled and as food additives (souring agents, etc.). More particularly speaking, it is usable for the following purposes, in addition to the deodorization method as described above: (1) sterilization of kitchen utensils and vegetables in kitchens, (2) sterilization in pickup points of vegetables, (3) sterilization of algae and miscellaneous germs in laver farms, (4) sterilization of meats, instruments, walls, floors, etc. in cattle meat plants, (5) addition of fumaric acid in juice manufacturing plants, (6) liquid bactericides for washing hands, (7) surface treatments of metals, (8) elimination of ammonia smell, (9) sterilization of cattle farms, etc.

In the present invention, a large amount of an aqueous fumaric acid solution can be obtained within a short time by passing water through a column packed with solid fumaric acid. It is also possible to obtain an aqueous fumaric acid solution with a high concentration. The process according to the present invention also makes it possible to produce an aqueous fumaric acid solution at a low cost.

Because of being made of a solid preparation containing fumaric acid which has a low solubility and a low dissolution rate in water, moreover, the deodorizing agent according to the present invention can deodorize an ammonia smell, etc. over a long period of time. It can also efficiently deodorize nitrogen-containing bad-smelling components in a urinal over a long period of time.

The present invention will be described in greater detail by reference to the following Examples, but it should be understood that the invention is not construed as being limited thereto.

Unless otherwise noted, all parts, ratios, percentages, etc. described herein are by weight.

PRODUCTION EXAMPLE 1

100 parts by weight of fumaric acid for food additives (manufactured by Takeda Chemical Industries; 24–200 mesh) was processed with a tabletting machine (manufactured by Applied Power Japan, ENERPAC PRE-SET PF-30-B) under a tabletting pressure of 5 t to give circular tablets each weighing 15 g (30 mm in diameter, 12 mm in height).

EXAMPLE 1

30 fumaric acid tablets obtained in the above Production Example 1 were packed into a cylindrical column (diameter: 100 mm, height: 102 mm, column volume: 0.83 l) and water was reversely passed through the column (i.e., from the bottom to the top) at a flow rate of 50 to 400 ml/min. Thus an aqueous fumaric acid solution wherein fumaric acid had been completely dissolved could be stably obtained. The thus obtained aqueous fumaric acid solution was free from solid fumaric acid and had a pH value of 2 to the column was capable of retaining 0.78 l of the solution and the packing volume was 0.74 l.

Table 1 shows the flow rate of water and the pH value the overflowing aqueous fumaric acid solution.

TABLE 1

| Water flow rate (ml/min) | pH change (min) | | | | | | | | | | |
|---|---|---|---|---|---|---|---|---|---|---|---|
| | 0 | 5 | 10 | 15 | 20 | 25 | 30 | 35 | 40 | 45 | 50 |
| 50 | 6.9 | 3.5 | 3.1 | 2.9 | 2.8 | 2.8 | 2.8 | 2.7 | 2.7 | 2.7 | 2.7 |
| 100 | 6.9 | 3.2 | 3.0 | 2.9 | 2.9 | 2.9 | 2.9 | 2.9 | | | |
| 200 | 6.9 | 3.2 | 3.0 | 3.0 | 3.0 | 3.0 | | | | | |
| 250 | 6.9 | 3.1 | 3.0 | 3.0 | 3.0 | | | | | | |
| 300 | 6.9 | 3.2 | 3.1 | 3.0 | 3.0 | | | | | | |
| 400 | 6.9 | 3.1 | 3.1 | 3.1 | | | | | | | |

PRODUCTION EXAMPLE 2

A mixture of 99 parts by weight of fumaric acid for additives (manufactured by Takeda Chemical Industries;

24–200 mesh) with 1 part by weight of sucrose ester was processed with a tabletting machine (manufactured by Hata Tekko) to give circular tablets each weighing 500 mg (10 mm iameter, 5 mm in height) and those each weighing 250 mg (10 mm in diameter, 2.5 mm in height).

EXAMPLE 2

3500 g of the fumaric acid tablets each weighing 500 obtained in the above Production Example 2 were packed into a cylindrical column (diameter: 100 mm, height: 500 mm, column volume: about 3.9 l) and tap water was reversely passed through the column (i.e., from the bottom to the top) at a flow rate of 100 to 500 ml/min. Thus an aqueous fumaric acid solution wherein fumaric acid had been completely dissolved could be stably obtained. The thus obtained aqueous fumaric acid solution was free from solid fumaric acid and had a pH value of 2 to 3. The packing height in the column was 380 mm and the packing volume was Table 2 shows the flow rate of water and the pH value of the overflowing aqueous fumaric acid solution.

TABLE 2

| Water flow rate | pH change (min) | | | | | |
| --- | --- | --- | --- | --- | --- | --- |
| (ml/min) | 10 | 20 | 30 | 40 | 50 | 60 |
| 100 | 2.8 | 2.7 | 2.6 | 2.6 | 2.5 | 2.5 |
| 200 | 2.9 | 2.8 | 2.8 | 2.7 | 2.8 | 2.7 |
| 300 | 2.8 | 2.8 | 2.8 | 2.8 | 2.8 | 2.7 |
| 400 | 2.9 | 2.8 | 2.7 | 2.7 | 2.7 | 2.7 |
| 500 | 2.9 | 2.9 | 2.8 | 2.9 | 2.8 | 2.7 |

PRODUCTION EXAMPLE 3

A mixture of 97 parts by weight of fumaric acid for additives (manufactured by Takeda Chemical Industries; 24–200 mesh) with 2 part by weight of sucrose ester and 1 part by weight of silicon dioxide (CARPLEX, manufactured by Shionogi & Co., Ltd.) was processed with a tabletting machine (manufactured by Hata Tekko) to give circular tablets each weighing 500 mg (10 mm in diameter, 5 mm in height) and those each weighing 250 mg (10 mm in diameter, 2.5 mm in height).

EXAMPLE 3

3500 g of the fumaric acid tablets each weighing 500 mg obtained in the above Production Example 3 were packed into a cylindrical column (diameter: 100 mm, height: 500 mm, column volume: about 3.9 l) and tap water was reversely passed through the column (i.e., from the bottom to the top) at a flow rate of 100 to 500 ml/min. Thus an aqueous fumaric acid solution wherein fumaric acid had been completely dissolved could be stably obtained. The thus obtained aqueous fumaric acid solution was free from solid fumaric acid and had a pH value of 2 to 3. The packing height in the column was 380 mm and the packing volume was 3 l.

Table 3 shows the flow rate of water and the pH value of the overflowing aqueous fumaric acid solution.

TABLE 3

| Water flow rate | pH change (min) | | | | | |
| --- | --- | --- | --- | --- | --- | --- |
| (ml/min) | 10 | 20 | 30 | 40 | 50 | 60 |
| 100 | 2.8 | 2.7 | 2.6 | 2.6 | 2.5 | 2.5 |
| 200 | 2.9 | 2.8 | 2.8 | 2.7 | 2.8 | 2.7 |
| 300 | 2.8 | 2.8 | 2.8 | 2.8 | 2.8 | 2.7 |
| 400 | 2.9 | 2.8 | 2.7 | 2.7 | 2.7 | 2.7 |
| 500 | 2.9 | 2.9 | 2.8 | 2.9 | 2.8 | 2.7 |

PREPARATION EXAMPLE 1

Fumaric acid for food additives (manufactured by Takeda Chemical Industries; 24–200 mesh) was processed with a tabletting machine to give circular tablets each weighing 15 g (30 mm in diameter, 12 mm in height).

PREPARATION EXAMPLE 2

A mixture of 99 parts by weight of fumaric acid for additives (manufactured by Takeda Chemical Industries; 24–200 mesh) with 1 part by weight of sucrose ester was processed with a tabletting machine (manufactured by Hata Tekko) to give circular tablets each weighing 500 mg (10 mm in diameter, 5 mm in height) and those each weighing 250 mg (10 mm in diameter, 2.5 mm in height).

EXAMPLE 4

210 rabbits were fed in a rearing room for experimental animals provided with shelves wherein water was intermittently flown from a washing water tank onto the rearing floor for 1 minute at intervals of 4 hours to thereby wash away the rabbits' feces. After the above washing operation, the ammonia concentration in the room was 3 ppm.

50 tablets (each weighing 15 g) containing 100% by weight of fumaric acid obtained in the above Preparation Example 1 were put into the washing water tank (volume: 200 l). After 4 hours, the pH value of the washing water was 2.9. Then the feces were washed away as described above with the use of the aqueous fumaric acid solution pooled in the tank. 5 minutes thereafter, the ammonia concentration in the room was lowered to 1 ppm or less. After repeating the above-described operation, no ammonia smell was noticeable in the room after 1 hour.

EXAMPLE 5

3 tablets (each weighting 15 g) containing 100% by weight of fumaric acid obtained in the above Preparation Example 1 were put on the outflow port of a urinal which was intermittently flushed after urination. Then the deodorization performance was examined over 1 month. As a result, any ammonia smell was scarcely noticeable and the urinal did not turned yellow during this period.

EXAMPLE 6

(1) 30 tablets (each weighing 15 g) containing 100% by weight of fumaric acid were put into a chemical drum (200 l). After supplying water thereinto, the mixture was slowly stirred and then allowed to stand for 5 hours. As a result, an aqueous solution having a pH value of 2.7 was obtained. The thus obtained aqueous fumaric acid solution was employed in washing a swine housing. Thus, the ammonia and amine smells were considerably relieved compared with the case wherein washing was performed with water alone.

(2) 3 tablets (each weighing 15 g) containing 100% by weight of fumaric acid were put into a polyethylene container (2000 ml). After supplying warm water (40 to 50° C.) thereto, the mixture was allowed to stand. After 5 hours, an aqueous solution having a pH value of 2.7 was obtained. The thus obtained aqueous fumaric acid solution was employed in washing a chopping board on which a fish had been cut. As a result, the amine smell was instantly eliminated and the miscellaneous germ count was largely reduced.

(3) 5 tablets (each weighing 15 g) containing 100% by weight of fumaric acid were put into a vinyl net (100-mesh) bag and then introduced into a polyethylene bucket containing 10 l of water. After allowing to stand for 5 hours, an aqueous solution having a pH value of 2.9 was obtained. The thus obtained aqueous fumaric acid solution was flown into an outflow port of waste water in a kitchen floor. As a result, the amine smell evolving from the outflow port was instantly eliminated.

(4) 50 tablets (each weighing 15 g) containing 100% by weight of fumaric acid were put into a tank of a tank type flush water closet (fecal tank volume: 100 l). After 1 hour, the ammonia and amine smells in the toilet were extremely relieved. After 3 days, the fecal volume amounted to 150 l. During this period, no ammonia/amine smell was noticeable. When the fecal volume amounted to 150 l, the contents of the tank were disposed.

(5) 300 tablets (each weighing 15 g) containing 100% by weight of fumaric acid were put into a cylindrical column (diameter 300 mm, height 600 mm) which was fitted to an outflow port for feces discharged from a swine housing. Then the liquid flowing from the port alone was passed through the column. As a result, the ammonia and amine smells of the fecal tank were significantly relieved.

While the invention has been described in detail and with reference to specific embodiments thereof, it will be apparent to one skilled in the art that various changes and modifications can be made therein without departing from the spirit and scope thereof.

This application is based on Japanese patent applications No. Hei.-10-367003, filed on Dec. 24, 1998, and No. Hei.-10-372785, filed on Dec. 28, 1998, herein incorporated by reference.

What is claimed is:

1. A deodorization method which comprises providing a column having an upper part and a lower part and having an inflow inlet in its lower part and an outflow outlet in its upper part, packing the column with a solid deodorizing agent comprising 70% by weight or more of fumaric acid, passing water through the column from the lower part inlet to the upper part outlet, and subsequently contacting a substance to be deodorized with said water.

2. The deodorization method as claimed in claim 1, wherein said substance to be deodorized comprises ammonia, an amine, or both of them.

3. The deodorization method as claimed in claim 1, wherein said deodorizing agent contains 70% by weight or more of fumaric acid.

4. The deodorization method as claimed in claim 1, wherein said deodorizing agent is in the form of tablets.

5. A deodorization method which comprises passing water through a column packed with solid fumaric acid and then flushing a urinal with the thus obtained aqueous fumaric acid solution.

6. A deodorization method which comprises contacting a substance to be deodorized with a deodorizing agent comprising an aqueous fumaric acid solution having a pH from 1 to 4.

7. The deodorization method of claim 6, wherein said deodorizing agent is placed in a urinal for deodorizing the same.

8. The deodorization method of claim 6, wherein said deodorizing agent is put into a tank or a tank type flush water closet for deodorizing the same.

9. The deodorization method of claim 6, wherein the pH is from about 2 to 3.

* * * * *